US010016134B2

(12) United States Patent
Hansen et al.

(10) Patent No.: US 10,016,134 B2
(45) Date of Patent: Jul. 10, 2018

(54) PORTABLE DEVICE AND METHOD OF COMMUNICATING MEDICAL DATA INFORMATION

(75) Inventors: Henrik Egesborg Hansen, Hellerup (DK); Michael Eilersen, Hvidorvre (DK); Niels Pryds Rolsted, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 720 days.

(21) Appl. No.: 12/796,373

(22) Filed: Jun. 8, 2010

(65) Prior Publication Data

US 2010/0250697 A1 Sep. 30, 2010

Related U.S. Application Data

(63) Continuation of application No. 12/017,369, filed on Jan. 22, 2008, now abandoned, which is a
(Continued)

(30) Foreign Application Priority Data

Aug. 13, 2001 (DK) .................................. 2001 01210

(51) Int. Cl.
*A61B 5/00* (2006.01)
*A61B 5/145* (2006.01)
(Continued)

(52) U.S. Cl.
CPC ............ *A61B 5/002* (2013.01); *A61B 5/0022* (2013.01); *A61B 5/14532* (2013.01);
(Continued)

(58) Field of Classification Search
USPC ................................................ 600/300–301
See application file for complete search history.

(56) References Cited

U.S. PATENT DOCUMENTS 4,407,295 A * 10/1983 Steuer et al. .................. 600/483
5,375,604 A * 12/1994 Kelly .................... A61B 5/0404
600/483
(Continued)

FOREIGN PATENT DOCUMENTS

| CA | 2210559 | 1/1998 |
| CN | 1174996 | 3/1998 |

(Continued)

OTHER PUBLICATIONS

Non-Final Office Action From U.S. Appl. No. 12/017,401, filed Jan. 22, 2008; Inventors: Hansen et al., dated Apr. 9, 2009.
(Continued)

*Primary Examiner* — William Thomson
*Assistant Examiner* — Shirley Jian
(74) *Attorney, Agent, or Firm* — Wesley Nicolas

(57) ABSTRACT

A portable medical device for communication of medical data information has a medical device part that includes a first processor and first storage means, and means for executing one or more medical related functions, a communication device part comprising a second processor, second storage means, and communication means. The medical device part and the communication device part are connected allowing for exchange of data information according to a predetermined protocol. The exchange of communication may be under the control of the medical device part, but the functionalities of each device part otherwise is separated providing for easy interchangeability of the communication device part or the medical device part. Also disclosed is a method for communication of medical data information.

23 Claims, 11 Drawing Sheets

Related U.S. Application Data continuation-in-part of application No. 10/216,680, filed on Aug. 7, 2002, now abandoned.

(60) Provisional application No. 60/315,085, filed on Aug. 27, 2001.

(51) Int. Cl.
*A61B 5/157* (2006.01)
*G06F 19/00* (2018.01)
*A61B 5/1468* (2006.01)
*H04W 88/02* (2009.01)

(52) U.S. Cl.
CPC .......... *A61B 5/157* (2013.01); *A61B 5/4833* (2013.01); *A61B 5/4839* (2013.01); *G06F 19/3418* (2013.01); *A61B 5/0017* (2013.01); *A61B 5/1468* (2013.01); *H04W 88/02* (2013.01)

(56) References Cited

U.S. PATENT DOCUMENTS

| | | | |
|---|---|---|---|
| 5,528,323 A | | 6/1996 | Fujieda et al. |
| 5,687,717 A * | | 11/1997 | Halpern et al. ............... 600/300 |
| 5,701,894 A * | | 12/1997 | Cherry et al. ................. 600/300 |
| 6,050,940 A * | | 4/2000 | Braun et al. .................. 600/300 |
| 6,093,146 A | | 7/2000 | Filangeri |
| 6,221,012 B1 * | | 4/2001 | Maschke ................ G06Q 50/24 600/301 |
| 6,297,738 B1 * | | 10/2001 | Newham .................... 340/573.1 |
| 6,380,858 B1 | | 4/2002 | Yarin et al. |
| 6,405,049 B2 * | | 6/2002 | Herrod .................. G06F 1/1626 455/517 |
| 6,417,857 B2 * | | 7/2002 | Finger ................. G01S 7/52023 345/505 |
| 6,478,736 B1 | | 11/2002 | Mault |
| 6,540,672 B1 * | | 4/2003 | Simonsen et al. ............ 600/300 |
| 6,571,128 B2 * | | 5/2003 | Lebel ..................... G16H 40/40 607/60 |
| 6,644,321 B1 * | | 11/2003 | Behm ........................... 128/899 |
| 6,648,822 B2 * | | 11/2003 | Hamamoto et al. .......... 600/300 |
| 6,712,762 B1 * | | 3/2004 | Lichter et al. ................ 600/300 |
| 6,790,178 B1 * | | 9/2004 | Mault .................. A61B 5/0011 128/903 |
| 6,804,558 B2 * | | 10/2004 | Haller et al. ..................... 607/30 |
| 6,809,653 B1 * | | 10/2004 | Mann .................. A61B 5/0002 340/870.28 |
| 6,958,691 B1 * | | 10/2005 | Anderson et al. ........ 340/539.12 |
| 7,103,380 B1 * | | 9/2006 | Ditzik ......................... 455/556.2 |
| 7,269,746 B1 * | | 9/2007 | Lada et al. ..................... 713/300 |
| 8,764,654 B2 * | | 7/2014 | Chmiel ............... G06F 19/3431 128/920 |
| 8,806,473 B2 * | | 8/2014 | Birtwhistle ............... G06F 8/65 340/5.6 |
| 2001/0029321 A1 | | 10/2001 | Beetz et al. |
| 2001/0051787 A1 * | | 12/2001 | Haller et al. ..................... 604/66 |
| 2002/0065540 A1 * | | 5/2002 | Lebel .................. A61N 1/37211 607/60 |
| 2002/0072932 A1 * | | 6/2002 | Swamy ............................. 705/2 |
| 2002/0091843 A1 * | | 7/2002 | Vaid ............................. 709/230 |
| 2002/0115913 A1 | | 8/2002 | Christ et al. |
| 2003/0055406 A1 * | | 3/2003 | Lebel et al. ................ 604/891.1 |
| 2003/0065536 A1 | | 4/2003 | Hansen et al. |
| 2003/0208113 A1 | | 11/2003 | Mault et al. |
| 2004/0176667 A1 * | | 9/2004 | Mihai et al. .................. 600/300 |
| 2005/0033124 A1 * | | 2/2005 | Kelly .................. G06F 19/3418 600/300 |
| 2006/0094936 A1 * | | 5/2006 | Russ ...................... H04M 1/725 600/300 |
| 2007/0027367 A1 * | | 2/2007 | Oliver .................. A61B 5/0002 600/300 |
| 2007/0073266 A1 * | | 3/2007 | Chmiel ................... A61B 5/00 604/503 |
| 2007/0179734 A1 * | | 8/2007 | Chmiel .................... A61B 5/00 702/127 |
| 2007/0255114 A1 * | | 11/2007 | Ackermann ............... G06F 8/65 600/300 |
| 2007/0299324 A1 * | | 12/2007 | Rasch-Menges .... A61B 5/0002 600/301 |
| 2008/0177155 A1 | | 7/2008 | Hansen et al. |
| 2008/0312585 A1 * | | 12/2008 | Brukalo ............ A61M 5/14244 604/67 |
| 2009/0171163 A1 * | | 7/2009 | Mates ...................... A61B 5/00 600/300 |
| 2009/0240117 A1 * | | 9/2009 | Chmiel ............... G06F 19/3431 600/301 |
| 2009/0290525 A1 * | | 11/2009 | Kekalainen ....... H04W 52/0216 370/313 |
| 2010/0047745 A1 * | | 2/2010 | Bergqwist .......... A61B 5/14532 434/127 |
| 2013/0173176 A1 * | | 7/2013 | Matsumura ............ G01N 33/66 702/19 |

FOREIGN PATENT DOCUMENTS

| | | |
|---|---|---|
| EP | 519137 A1 | 12/1992 |
| EP | 0770349 A1 | 12/1992 |
| EP | 0903709 | 3/1999 |
| EP | 970655 A1 | 1/2000 |
| EP | 1395170 A1 | 3/2004 |
| JP | H0975310 A | 3/1997 |
| JP | 11-8707 | 1/1999 |
| JP | 2001061794 A | 3/2001 |
| JP | 2002109664 A | 4/2002 |
| WO | WO 9959657 | 11/1999 |
| WO | WO 0032088 | 6/2000 |
| WO | WO 0032258 | 6/2000 |
| WO | WO 00/47109 | 8/2000 |
| WO | WO 0050971 | 8/2000 |
| WO | WO 00/62662 | 10/2000 |
| WO | WO 0121690 A2 | 1/2001 |
| WO | WO 0139089 | 5/2001 |
| WO | WO 01/52934 | 7/2001 |
| WO | WO 01/52935 | 7/2001 |
| WO | WO 01/54753 | 8/2001 |

OTHER PUBLICATIONS

Final Office Action From U.S. Appl. No. 12/017,401, filed Jan. 22, 2008: Inventors:.Hansen et al., dated Dec. 10, 2009.
Non-Final Office Action From U.S. Appl. No. 12/017,369, filed Jan. 22, 2008; Inventors: Hansen et al., dated Apr. 15, 2009.
Final Office Action From U.S. Appl. No. 12/017,369, filed Jan. 22, 2008; Inventors: Hansen et al., dated Dec. 11, 2009.
Office Action Issued in Counterpart Japanese Application No. 2003-520792, dated Mar. 17, 2009.
Office Action Issued in Counterpart Chinese Application No. 02815916.0 dated Jan. 4, 2008.
Lortz et al., "What Is Bluetooth? We Explain the Newest Short-Range Connectivity Technology," 2002, Sandhill Publishing, Smart Computing Learning Series Wireless Computing, pp. 72-74.
Design Control Guidance for Medical Device Manufacturers, Dated Mar. 11, 1997 (Obtained From http://www.fda.gov/cdrh/comp/designgd.pdf).
General Principles of Software Validation: Final Guidance for Industry and FDA Staff, Dated Jan. 11, 2002 (Obtained From http://www.fda.gov/cdrh/comp/guidance/938.pdf).
English Language Abstract of JP 2001-061794 A.
English Language Abstract of JP 2002-109664 A.
Search Report Issued in Connection With Counterpart PCT Application No. PCT/DK02/00529, dated Nov. 28, 2002.
Search Report Issued in Connection With Counterpart PCT Application No. PCT/DK02/00529, dated Apr. 3, 2003.
Written Opinion Issued in Connection With Counterpart PCT Application No. PCT/DK02/00529, dated Sep. 26, 2003.
Office Action Issued in Connection With Counterpart Russian Application No. 2004107509(008007) Filed Aug. 12, 2002, dated Jul. 12.

(56) References Cited

OTHER PUBLICATIONS

Office Action Issued in Connection With Counterpart Russian Application No. 2004107509/14(008007), dated Aug. 13, 2007.
Office Action Issued in Connection With Counterpart Chinese Application No. 02815916.0, dated Dec. 1, 2006.
Office Action Issued in Connection With Counterpart Chinese Application No. 02815916.0, dated Aug. 3, 2007.
Office Action Issued in Connection With Counterpart Australian Application No. 2002355886, dated Dec. 8, 2006.
Search Examination Report Issued in Connection With Counterpart Indian Application No. 296/CHENP/2004, dated Mar. 5, 2007.
United States Food and Drug Administration. "Design Control Guidance for Medical Device Manufacturers" Mar. 11, 1997.
United States Food and Drug Administration "General Principles of Software Validation; Guidance for Industry and FDA Staff." Jan. 11, 2002.

* cited by examiner

PORTABLE DEVICE AND METHOD OF COMMUNICATING MEDICAL DATA INFORMATION

CROSS REFERENCE TO RELATED APPLICATIONS

This application is a Continuation of U.S. Non-Provisional application Ser. No. 12/017,369 (filed Jan. 22, 2008), which is a Continuation-In-Part of U.S. Non-Provisional application Ser. No. 10/216,680 (filed on Aug. 7, 2002), and which claims the benefit of priority under 35 USC § 119 of U.S. Provisional Application 60/315,085 (filed on Aug. 27, 2001) and Danish Application PA 2001 01210 (filed Aug. 13, 2001), all of which are hereby incorporated by reference in their entirety.

BACKGROUND OF THE INVENTION

Field of the Invention

The present invention relates to a portable medical device for communication of medical data information.

The present invention also relates to a method of communication of medical data information by a portable medical device.

Related Art

Product and software validation for medical products are troublesome, delays a product's time-to-market, time-consuming, complicates revision tasks, and is expensive.

For example, in some jurisdictions, regulatory bodies govern the approval of medical products (e.g., devices) according to preset validation standards for medical products. Likewise, regulatory bodies typically also govern the approval of any software contained within medical products according to preset validation standards for medical product software. For example, in the United States the Food and Drug Administration (FDA) has issued a document entitled, "Design Control Guidance for Medical Device Manufacturers," on Mar. 11, 1997, which provides criteria for approval of medical product (e.g., device) design according to its established preset validation standards. Likewise, with regard to software, the FDA has issued a document entitled "General Principles of Software Validation; Final Guidance for Industry and FDA Staff" on Jan. 11, 2002 (which supersedes an earlier document dated Jun. 9, 1997), which provides criteria for approval of software according to its established preset validation standards.

Medical products (e.g., devices) can further include communication parts (e.g., Bluetooth, Radio frequency (RF) communication, Infrared (IR) communication, HTTP (Hyper Text Transmission Protocol), SHTTP (Secure Hyper Text Transmission Protocol), TCP/IP (Transmission Control Protocol/Internet Protocol), PPP (Point-to-Point), SSL (Secure Socket Layer), TLS (Transport Layer Security), GSM (Global System for Mobile communication), GPRS (General Packet Radio System), UMTS (Universal Mobile Telephone System), and IrDA, among others) of which the general design and operation of the communication parts are governed and/or regulated by standards setting bodies which provide criteria for approval of communication parts according to established preset validation standards.

It has heretofore been known to fully integrate communication parts and software within the medical products, such that approval of each of the communication part, the medical product (e.g., device), and the software is required, each according to preset validation standards in their appropriate technology and/or jurisdiction. However, the full integration of the communication part or software within the medical product can require renewed approval of the entire medical product (i.e., device and software) if any revisions are made to either the communication part, medical product (e.g., device) itself, or any software contained in the medical product. Thus, revisions of either the communication part, medical product (e.g., device) or any software contained in the medical product can delay a product's time-to-market, be time-consuming, complicates revision tasks, and can be expensive.

Rapid development in the field of communication requires for frequent updates of communication soft-, hard- and/or firmware in a medical device. As a result medical product and software validation is required for a medical device with updated communication means even though no changes have been made to the medical application "part" of the device.

SUMMARY OF THE INVENTION

In view of the above disadvantages, the present invention provides a method and device that avoids the need for further medical product validation (e.g., by jurisdictional regulatory bodies) when the communication part and/or software of a medical device is changed, updated, or revised.

Likewise, the present invention provides a method and device that avoids the need for further software validation (e.g., by jurisdictional regulatory bodies) when the medical product (e.g., device) and/or communication part is changed, updated, or revised.

The present invention further provides a method and device that avoids the need for further communication part validation (e.g., by standards setting bodies) when the medical product (e.g., device) and/or software of a medical device is changed, updated, or revised.

The present invention further provides for clearly separate critical medical application functionalities from the complex communication software, hardware and/or firmware in order to obtain maximum safety and reliability of the critical medical application.

The present invention can be achieved by a device of the aforementioned kind that comprises:
   a medical device part comprising:
   a first processor and first storage means, and
   a means for executing one or more medical related functions,
   a communication device part comprising:
   a second processor, second storage means, and
   a communication means,
   wherein the medical device part and the communication device part is connected allowing for exchange of data information according to a predetermined protocol, the exchange of data information is under the control of the medical device part and where the functionalities of each device part otherwise is separated.

Hereby, two physically and functionally separated parts/units are obtained where one part is a medical device part responsible for performing medically related actions, measurements, calculations, exchange of data with other medical devices, etc. and another part is a communication device part (just communication part in the following) responsible for receiving and transmitting information under the control of the medical device. The medical device part controls the communication so the communication part cannot interrupt or request service(s) from the medical device part, thereby ensuring maximum safety and reliability of the medical application(s).

In this way, when the parts (software, hardware, firmware, etc.) of the communication device needs to be upgraded, the integrity of the medical device part is preserved and the need for any further medical product and software validation is avoided thereby reducing time-to-market, expenses, etc.

Furthermore, when changes to the medical device part hardware, software, and/or firmware are required then the scope of medical product and software validation can be restricted to the medical device part and need not involve the communication device part thereby simplifying revisions tasks, etc.

According to a preferred embodiment, the predetermined protocol comprises the medical device part acting as a master and the communication device part acting as a slave where the exchange of information is done by the medical device part polling the communication device part.

In this way, a simple protocol may handle and connect the two asynchronous systems/parts of the medical device in a very simple fashion and the communication part cannot interfere, interrupt and/or transmit data/information to the medical part without its permission.

In one embodiment, the medical device part further comprises one or more of:
  a user interface,
  at least one medical transducer,
  discrete and/or substantially continuously body fluid analysis means,
  drug administration means, and
  a short-range communication means for exchanging data information with at least another medical device.

In this way, relevant medical functions, like blood glucose/body fluid level measurement(s), drug or insulin administration, may be integrated directly with the medical device, so that a user will always have a medical function ready at hand when using the medical device thereby avoiding the need for an extra medical device. Additionally, the medical device may act as a data collection/exchange device collecting/exchanging data with other relevant medical devices using short-range communication.

In one embodiment, the at least another medical device is selected from the group of:
  a drug administration device,
  a body fluid analyser,
  an insulin administration device,
  a blood glucose monitor (BGM),
  a continuous blood glucose monitor (CGM),
  an inhaler,
  a tablet dispenser,
  a lipid monitor,
  a pulse monitor,
  a lancet device,
  a storage container,
  a balance,
  and any other apparatus adapted to measure at least one physiological parameter.

In one embodiment, the device further comprises a power supply supplying the communication device part with power where the power supply may be turned on and off under the control of the medical device part.

In this way, power usage may be saved/minimized by turning the communication part off when it is not used which is especially important for portable devices usually having a limited power supply.

In one embodiment, the communication means is adapted to communicate according to the Bluetooth protocol.

Hereby, a very simple way of connecting to other devices and/or networks are obtained.

In one embodiment, the communication means are adapted to communicate information according to one or more of:
  Radio frequency (RF) communication,
  Infrared (IR) communication,
  HTTP (Hyper Text Transmission Protocol),
  SHTTP (Secure Hyper Text Transmission Protocol),
  TCP/IP (Transmission Control Protocol/Internet Protocol),
  PPP (Point-to-Point),
  SSL (Secure Socket Layer),
  TLS (Transport Layer Security), and
  IrDA, In one embodiment, the communication means are adapted to communicate with a wireless access point/a mobile terminal where the access point/the terminal is adapted to communicate according to one or more of:
  GSM (Global System for Mobile communication),
  GPRS (General Packet Radio System), and
  UMTS (Universal Mobile Telephone System).

In this way, a great level of mobility is assured for the user of the medical device as well as being able to transmit relevant data information.

In one embodiment, the communication device part is adapted to exchange data information with a central server via a wireless network access point.

The invention also relates to a system for supplying data from a portable medical device to a third party, where the system is adapted to:
  automatically transmit data information from a portable medical device to a central server for storage in at least one database,
  process said data information, in order to derive additional information, and
  automatically transmit at least a part of the additional information to a predetermined third party.

In this way, a relative/relatives may obtain an ease at mind since they know that they will receive information if anything is wrong or may be potentially dangerous or they simply is automatically updated on the user's current situation. This is especially useful for relatives of elderly people, children, etc. using a medical device. A medical professional may also receive relevant information in this manner.

In one embodiment, the processing is done at said server and/or at said medical device.

In one embodiment, the data information comprises information representing one or more of:
  at least one blood glucose value,
  at least one value representing a body fluid level,
  at least one physiological parameter,
  amount and/or type of administered medication,
  amount and/or type of administered insulin,
  a trend of a glucose or body fluid level,
  a prediction of a glucose or body fluid level,
  timestamp in- or excluding date,
  amount of food,
  measurement of physical activity,
  notification of appointment,
  inventory logistics, and
  body characteristics.
  warnings, and
  symptoms.

In one embodiment, the system is adapted to transmit data information from a portable medical device to a central server according to the Bluetooth protocol using a wireless access point connected via a network to the central server.

In one embodiment, the third parties are one or more of:

at least one relative,
at least one parent, and
at least one medical professional.

In one embodiment, the system is further adapted to exchange information between the portable medical device and another medical device in order to retrieve relevant data information.

The invention also relates to a system for collecting data information from a number of portable devices, wherein the system is adapted to:
generate data information in a portable device, the data information relating to a clinical trial of a medical device and/or medical product,
automatically sending the data information from the portable device to a central server for storage in a database, and
process said data information.

In this way, relevant information may then be automatically transmitted directly to a relevant server for high-quality data storage and collection since the actual obtained data is obtained directly from the user/patient and transmitted e.g. for further processing. This may reduce the cost and the time-to-market of a new product since the data collection from many medical devices taking part in the medical trial may be automated. Additionally, the need for hand-written logs of the participants of the trial is avoided thereby eliminating possible typos and avoiding the need for manually inputting/scanning the logs into a system for storage and processing.

The invention also relates to a method of communication of medical data information between
a medical device part comprising:
a first processor and first storage means, and
a means for executing one or more medical related functions, and
a communication device part comprising:
a second processor, second storage means, and
a communication means,
wherein the medical device part and the communication device part exchanges data information according to a predetermined protocol, the exchange of data information is under the control of the medical device part and where the functionalities of each device part otherwise is separated.

In one embodiment, the predetermined protocol comprises the medical device part acting as a master and the communication device part acting as a slave where the exchange of information is done by the medical device part polling the communication device part.

In one embodiment, the medical device part further comprises one or more of:
a user interface,
at least one medical transducer,
discrete and/or substantially continuously body fluid analysis means,
drug administration means, and
a short-range communication means for exchanging data information with at least another medical device.

In one embodiment, the at least another medical device is selected from the group of:
a drug administration device,
a body fluid analyser,
an insulin administration device,
a blood glucose monitor (BGM),
a continuous blood glucose monitor (CGM),
an inhaler,
a tablet dispenser,
a lipid monitor,
a pulse monitor,
a lancet device,
a storage container,
a balance, and
any other apparatus adapted to measure at least one physiological parameter.

In one embodiment, the method further comprises controlling a power supply by the medical device part, where the power supply supplies the communication device part with power.

In one embodiment, said communication means communicates according to the Bluetooth protocol.

In one embodiment, said communication means communicates information according to one or more of:
Radio frequency (RF) communication,
Infrared (IR) communication,
HTTP (Hyper Text Transmission Protocol),
SHTTP (Secure Hyper Text Transmission Protocol),
TCP/IP (Transmission Control Protocol/Internet Protocol),
PPP (Point-to-Point),
SSL (Secure Socket Layer),
TLS (Transport Layer Security), and
IrDA, In one embodiment, said communication means communicates with a wireless access point/a mobile terminal where the access point/the terminal communicates according to one or more of:
GSM (Global System for Mobile communication),
GPRS (General Packet Radio System), and
UMTS (Universal Mobile Telephone System).

In one embodiment, the communication device part exchanges data information with a central server via a wireless network access point.

The invention also relates to a method of supplying data from a portable medical device to a third party, the method comprising the steps of:
automatically transmitting data information from a portable medical device to a central server for storage in at least one database,
processing said data information, in order to derive additional information, and
automatically transmitting at least a part of the additional information to a predetermined third party.

In one embodiment, said processing is done at said server and/or at said medical device.

In one embodiment, said data information comprises information representing one or more of:
at least one blood glucose value,
at least one value representing a body fluid level,
at least one physiological parameter,
amount and/or type of administered medication,
amount and/or type of administered insulin,
a trend of a glucose or body fluid level,
a prediction of a glucose or body fluid level,
timestamp in- or excluding date,
amount of food,
measurement of physical activity,
notification of appointment,
inventory logistics, and
body characteristics.
warnings, and
symptoms.

In one embodiment, said step of transmitting data information from a portable medical device to a central server is done by transmitting said data information according to the Bluetooth protocol using a wireless access point connected via a network to the central server.

In one embodiment, said third parties are one or more of:
   at least one relative,
   at least one parent, and
   at least one medical professional.

In one embodiment, said method further comprises the step of communicating between the portable medical device and another medical device in order to retrieve relevant data information.

Finally, the invention also relates to a method of collecting data information from a number of portable devices, the method comprising the steps of:
   generating data information in a portable device, the data information relating to a clinical trial of a predetermined medical product and/or device,
   automatically sending the data information from the portable device to a central server for storage in a database, and
   processing said data information.

The method and embodiments thereof correspond to the device and embodiments thereof and have the same advantages for the same reasons, and therefore will not be described again.

DETAILED DESCRIPTION OF THE INVENTION

Figure 1:
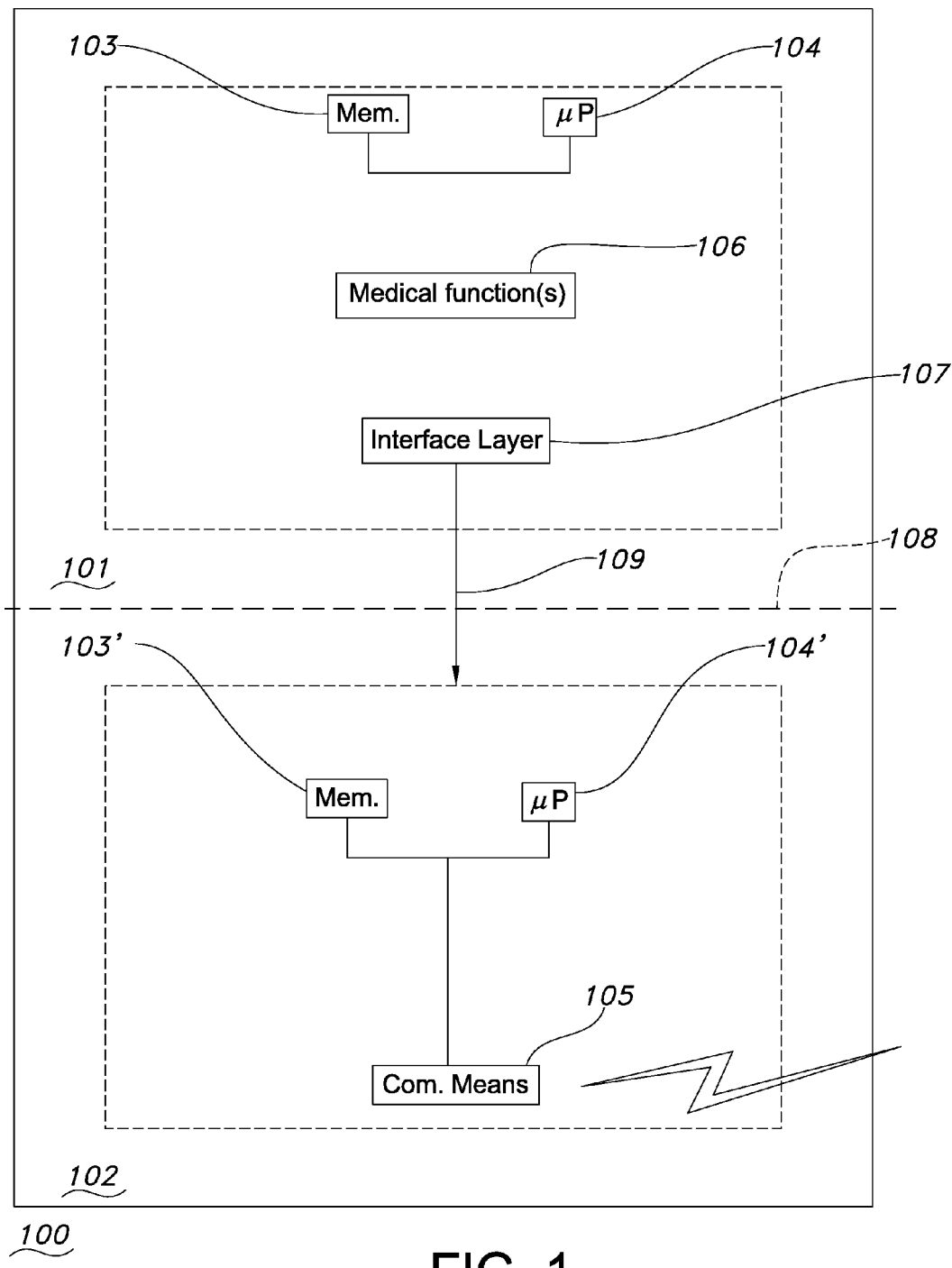
FIG. 1 shows a schematic block diagram of a medical device according to the present invention.

FIG. 1 shows a schematic block diagram of a medical device according to the present invention. Shown is a medical device (100) comprising an integrated medical device part (101) (denoted medical part in the following) and an integrated communication device part (102) (denoted communication part in the following).

The medical part (101) comprises one or more first microprocessors/processing means (104), a first storage/storage means/memory means (103), and means for providing/performing medical related functionalities (106) like medically related actions, measurements, calculations, etc.

The means for providing medical functionalities (106) may e.g. comprise one or more of body fluid analyser means, drug administration means, and/or short-range communication means for communicating with at least another medical device and may operate under the control of a separate processor (not shown), again being controlled by the first processor (104), or under the control of the first processor (104) directly.

The communication part (102) comprises one or more second microprocessors/processing means (104'), a second storage/storage means/memory means (103'), and communication means (105) for communicating with and/or via other devices.

The medical part (101) and the communication part (102) are connected allowing for exchange of date between them via a physical interface (like a simple electrical connection) where the exchange of data happens according to an interface layer (107) located in and under the control of the processor (104). The interface layer (107) comprises a suitable protocol and is under the complete control of the processor (104) of the medical part (101). A suitable protocol may e.g. be a protocol where the medical part (101) operates as a master and the communication part (102) operates as a slave as indicated by the one-way arrow (109) (even though exchange of information is allowed in both directions). In this way, two physically and functionally separated parts/units (101; 102) are obtained as indicated by the line (108) where a medical part (101) is responsible for performing medically related actions, measurements, calculations, etc. and another part (102) is a communication part responsible for receiving and transmitting information under the control of the medical device. Hereby, the critical medical application functionalities is clearly separated from the complex communication software, hardware and/or firmware giving maximum safety and reliability of the critical medical application.

Preferably, the medical device (100) further comprises a user interface (not shown) for receiving and/or presenting information from/to a user of the medical device (100). The user interface preferably comprises input means like buttons, scroll-wheels or the like and output means like a display or combined input-output means like a touch sensitive display like already known in the art.

The first and second storage/memory means (103; 103') may e.g. be a non-volatile memory, a volatile memory or a combination of both. Examples are flash memory, RAM, ROM, EEPROM, magnetic and/or optic storage means, etc.

The first (104) and second (104') processing means/processors may comprise one or more general or special purpose micro-processors or a mix hereof.

The communication means (105) preferably communicates according to the Bluetooth standard/protocol. Alternatively, communication via RF, IR, a wire/cable is used according to a suitable protocol.

Figure 2:
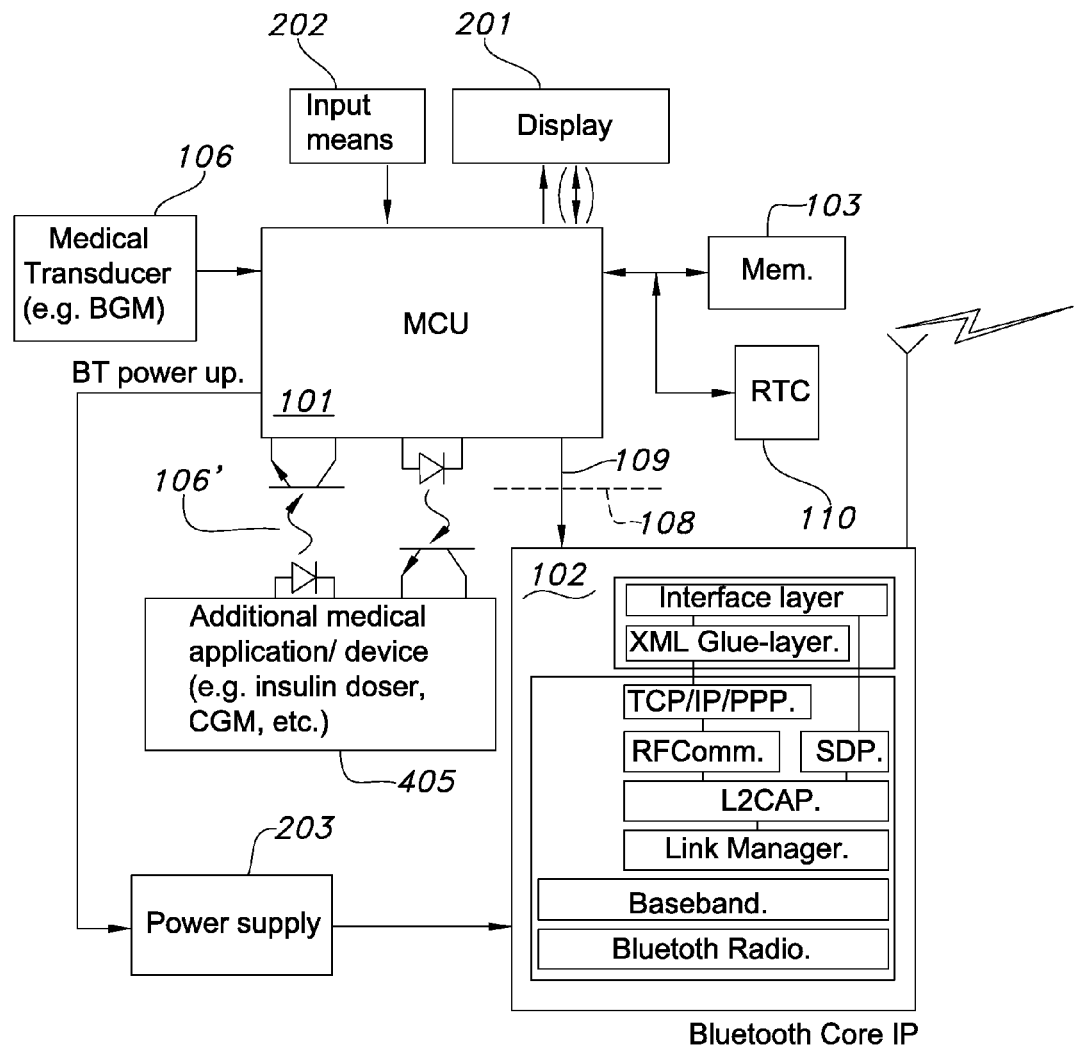
FIG. 2 shows a more detailed schematic block diagram of a medical device comprising a Bluetooth communication device part.

FIG. 2 shows a more detailed schematic block diagram of a medical device comprising a Bluetooth communication part. Shown is a medical part (101) and a communication part (102) corresponding to the one shown in FIG. 1.

The communication part (102) comprises a Bluetooth communication core and is adapted to communicate with external devices according to the well-known Bluetooth protocol. The Bluetooth core/the Bluetooth protocol stack comprises an Interface Layer interfacing with the medical part (101). The Interface Layer comprises in one embodiment an XML Glue-layer for generating, providing, handling, etc. XML scripts thereby allowing for a receiver to handle/execute these scripts directly. The protocol stack of the communication part (102) also comprises the TCP/IP (Transmission Control Protocol/Internet Protocol) and PPP (Point-to-Point Protocol) protocols connected to the Interface Layer via the XML Glue-layer. An RFComm (a serial emulation protocol) manager is connected to the TCP/IP/

PPP protocol manager. The Bluetooth Core also comprises a Service Discovery Protocol (SDP) manager that is responsible to determine which services are available from Bluetooth enabled service servers like a PC or a mobile telephone offering services like Internet and/or Network connection, etc. or other types of services. The SDP manager is also connected to the Interface Layer. Both the SDP and the RFComm manager are connected to a L2CAP (Logical Link Control and Adaption Protocol) manager (responsible for channel establishment) that is connected to a Link Manager (LM) (responsible for link establishment). The Bluetooth Core also comprises a Baseband and a Bluetooth Radio specification responsible for the radio communication according to the Bluetooth specification. Information regarding the Bluetooth protocol may e.g. be obtained at www.bluetooth.com incorporated herein by reference.

The communication steps between the medical device part (101) and a communication part (102) using Bluetooth are explained in greater detail in connection with FIG. 3.

The medical part (101) comprises a user interface for receiving and/or presenting information from/to a user of the medical device in the form of input means (202) like buttons, scroll-wheels, etc. and output means like a display (201) or combined input-output means like a touch sensitive display as signified by the double arrow in parenthesis. The medical part (101) also comprises a memory (103) for storing software, firmware, relevant data/information, etc. The medical part also comprises a real-time clock (RTS) (110) for enabling time- and date-stamps of generated/provided information like time-stamping a glucose/body fluid level measurement, a drug/insulin administration, etc.

Furthermore, the medical part (103) comprises one or more medical function(s) (106) like described in connection with FIG. 1. In this particular embodiment the medical device part (101) comprises an integrated medical transducer or a medical potentiostat like a body fluid analyser or more particularly a BGM (blood glucose monitor), either a continuous (CGM) or a discreet monitor. An additional medical function in this particular embodiment is (e.g. very) short-range communication means (106') so that the medical device part (101) may communicate with another medical device (405), like a drug administration unit, an insulin pen, an insulin doser, an inhaler, tablet dispenser, etc., in a very simple manner thereby allowing exchange of relevant information/data like type and amount/dose of administered medication and a corresponding time/date-stamps. The information may e.g. be generated during use of the other medical device(s) and stored there until transferred to the medical part (101). These short-range communication means may e.g. be optically communication means like a Infrared transmitter/receiver pair (106') where communication is initiated automatically when the additional medical device is docked with or fitted to the medical communication device (100) or simply is in close proximity. Alternative short-range communications means are inductive or electronic communications means that are explained in greater detail in connection with FIGS. 7a-7c.

Alternatively, the communication part (102) may be used to exchange information with other medical devices (405) thereby avoiding the need for short-range communications means (106'), however the short-range communications means (106') would typically require less power and allows for simple, easy and transparent, for the user, (if communication is initiated when docking the device) exchange of information.

The medical device part (101) and communication part (102) are separated like described before and signified by the line (108) and connected allowing only for exchange of data under the strict control (as signified by the one-way arrow (109)) of the medical device part (101).

The medical device preferably also comprises a power supply (203) to the communication part (102) that is controlled by the medical device part (101). In this way, the communication part (102) may be turned off in order to conserve power.

Figure 3:
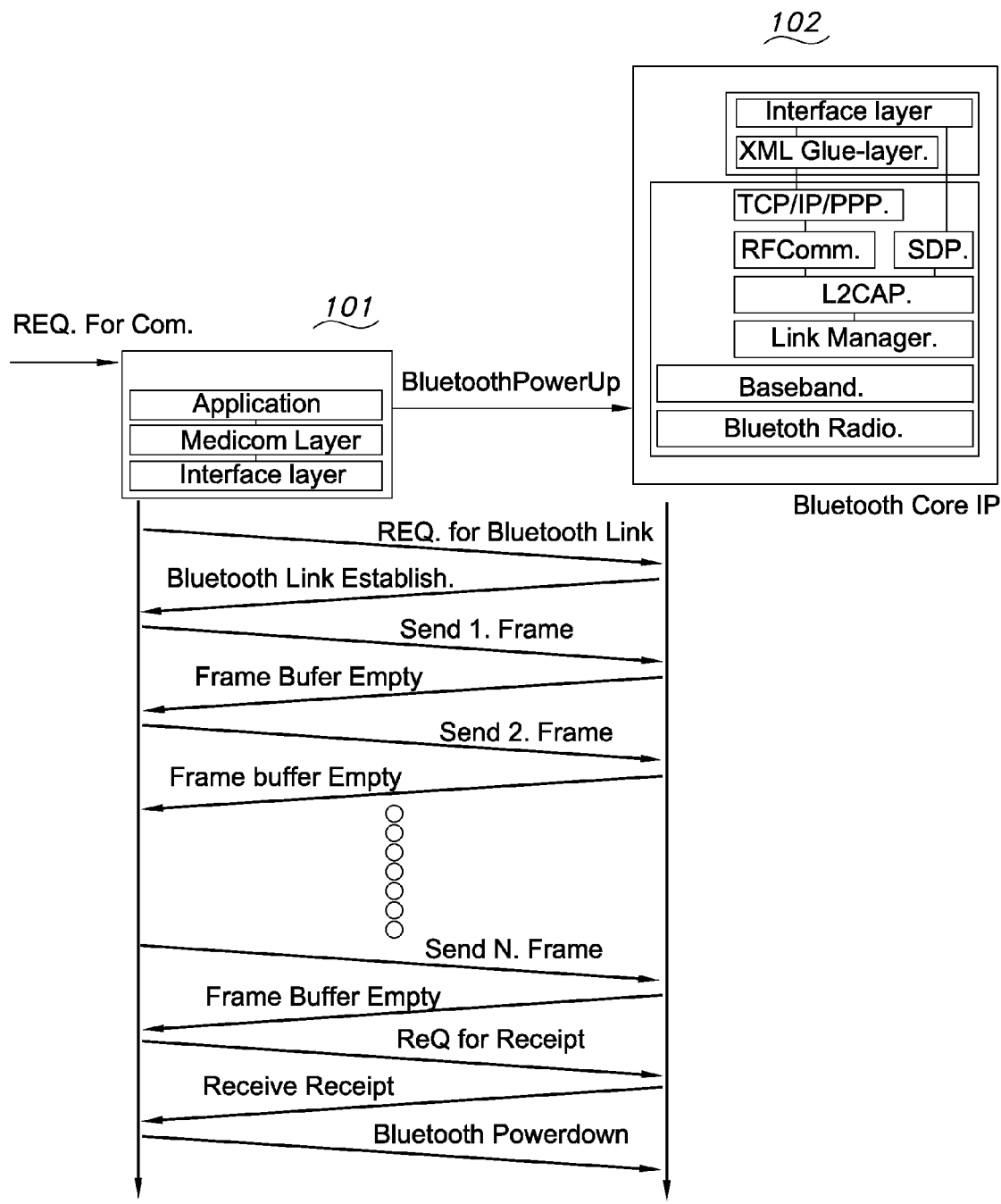
FIG. 3 illustrates the communication between a medical device part and a Bluetooth communication device part.

FIG. 3 illustrates the communication between a medical part and a Bluetooth communication part. Shown are the communication steps between the medical device part (101) and the communication device part (102).

The medical device part (101) comprises an application layer, a Medicom Layer (corresponds to (106) in FIGS. 1 and 2) and an Interface Layer (corresponds to (107) in FIG. 1). The medical device part (101) comprises the Bluetooth core shown and described in connection with FIG. 2.

Communication may e.g. be initiated either on user request, request by a medical application in the medical device part (101) (e.g. on the basis of an obtained measurement from an integrated medical transducer), an internal request by the medical device (100), by docking another medical device with the medical device (100) and/or using short-range communication means (106') with an additional medical device like a doser, a CGM, inhaler, a BGM, etc.

When a request for Bluetooth communication via the communication device part (102) is generated, the medical part (101) generates a Bluetooth power-up by activating the power supply (203 in FIG. 2) if the communication part (102) is not already powered. Then a request for a Bluetooth link to a relevant information receiver is sent to the communication part (102). The communication part (102) establishes a suitable link and returns an acknowledgement after which the actual communication/transmission of data may begin. If no establishment of a communication link is possible or communication is impossible for another reason, the relevant information is kept and may be tried transmitted at another time, e.g. when the user uses the medical device (100) the next time. Preferably, the communication part (102) is switched off when it is determined that no communication is currently possible in order to conserve power usage. A warning may be presented to the user specifying that communication was not possible, but preferably the communication takes place without the user's specific knowledge and a warning may e.g. only be presented to the user if no data communication was possible after a given number of tries or within a given period of time dependent on the actual application of the medical device (100).

After a Bluetooth link is successfully established, a first frame comprising an amount of data/information is sent to the communication part (102) where the frame is transmitted via the Bluetooth radio transmitter. The communication part (102) reports when the information has been transmitted, i.e. when a frame buffer is empty. The steps 'send frame' and 'report empty buffer' repeats/loops until the complete amount of information has been sent, i.e. N frames of information has been transmitted via Bluetooth radio communication. After the medical part (101) receives a 'frame buffer empty' and no further information has to be sent, the medical part (101) may send a request for receipt of the Bluetooth communication from the communication part (102). The communication part (102) returns a receipt of the Bluetooth communication with the relevant information receiver to the medical device part (101), which then executes a power-down of the communication part (102) in order to conserve power if no additional information is to be exchanged.

The communication between the communication part (102) and a relevant information receiver is explained in connection with FIGS. 4a, 4b and 5.

Figure 4A:
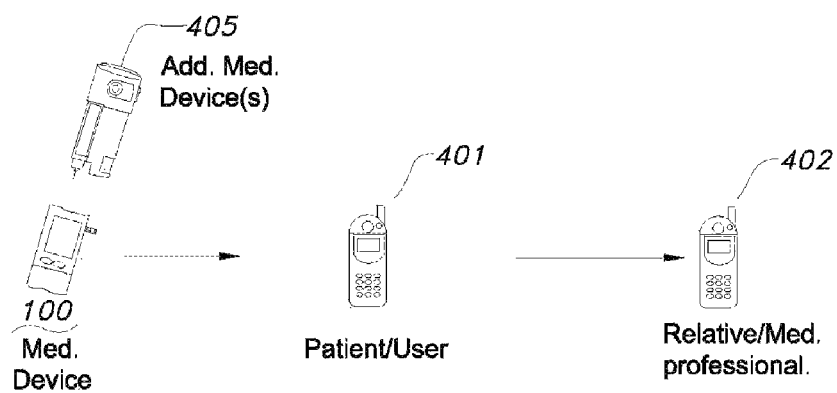
FIGS. 4a and 4b illustrates examples of the communication between a medical device and other devices according to the present invention.
Figure 4B:
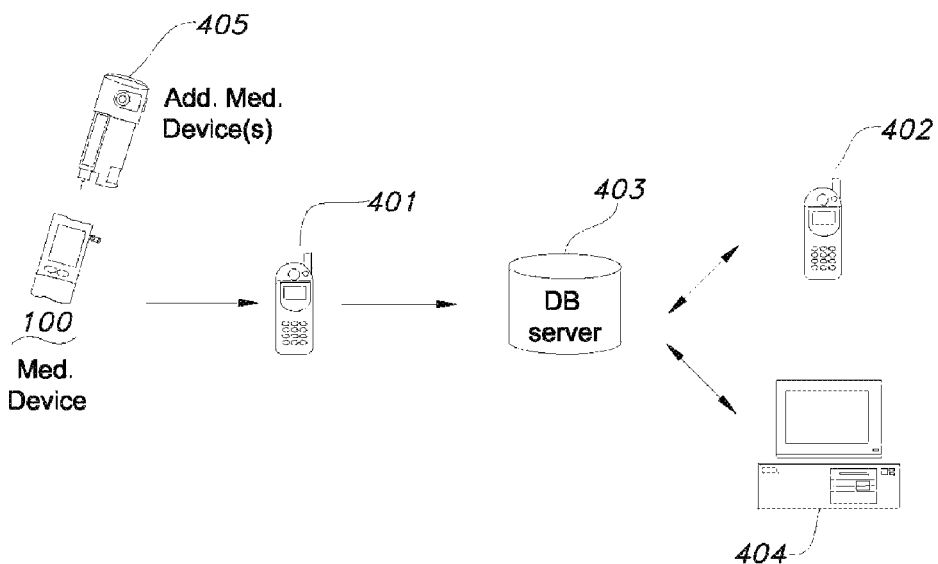

FIGS. 4a and 4b illustrates examples of the communication between a medical device and other devices according to the present invention.

FIG. 4a illustrates communication between a medical device (100) and a mobile communications terminal (402) belonging to a relevant third party via a mobile communications terminal/a wireless access point (401), belonging to a user of the medical device (100), to a network/the Internet. The medical device (100) preferably communicates with the user terminal (401) according to the Bluetooth protocol like described in connection with FIGS. 2 and 3, thereby establishing a Bluetooth communications link between the communication device part of the medical device (100) and the user's terminal (401). Alternatively, the communication between the medical device (100) and the user's terminal (401) may be done via IR communications means, a cable connecting them, other radio frequency (RF) communications means, etc.

When the Bluetooth communications link is established information may be transmitted to a terminal (402) of a relevant third party using a GSM (Global System for Mobile communication), UNITS (Universal Mobile Telephone System) and/or GPRS (General Packet Radio System) communication network or another wireless communication network, so that relevant information may be exchanged between the user's terminal (401) (and thereby the medical device (100)) and the terminal (402). The information may e.g. be exchanged between the terminal (401) and the terminal (402) using SMS (Short Message Service) or e-mail as a carrier (e.g. sending SMS messages/e-mails alternating in both or in one direction only) or alternatively, a two-way data communication between the terminals (401; 402).

A relevant third party may e.g. be a medical professional, a care-team, etc. and/or a relative of the user.

In this way, a medical professional may, e.g. automatically, receive status reports of the user at a regular time interval or when dangerous or potentially dangerous situation occurs or is about to occur, e.g. when a critical body fluid/blood glucose level being outside a predetermined interval has been determined and/or estimated (for a future time) by the medical device (100). Additionally, the professional may send relevant information, like an updated medical regime and/or target body fluid/blood glucose level interval, suggested action for a given situation (e.g. administer X amounts of type Y medication) e.g. in response to information/data received from the user's terminal (401)/the medical device (100). This enables a very close and precise monitoring of the user since data/information may be transmitted to a professional regularly in an easy and transparent manner and the data/information may be obtained directly by the medical device (100) and/or other devices (BGM, CGM, insulin doser, drug administration device, body fluid monitor, etc.) in communication and/or integrated with the medical device (100).

A medical professional may also determine when the user has to be called in for a consultation, check-up, etc. based on actual received information instead of having regular consultations. In this way, a user only needs to attend a consultation when there is an actual need. Additionally, the professional is better prepared since the relevant information is available to him in advance of an consultation.

Another application of the present invention is that one or more relatives of the user of the medical device (100) automatically may receive a status report or information from the medical device (100) via the terminal (401) regarding how the user's situation is and/or going to be in the near future. The transmitted information may e.g. contain time/date, type and/or amount of administered medication, time/date and value of performed measurement(s), compliance with a medical regime, etc. or simply just a status e.g. 'Status is ok', 'possible problem(s)', 'Serious problems', 'X follows the medical regime fully', 'X has a BGL within the target range', etc.

In this way, a relative/relatives obtains an easy at mind since they know that they will receive information if anything is wrong or may be potentially dangerous or they simply is automatically updated on the user's current situation. This is especially useful for relatives of elderly people, children, etc. using a medical device (100).

The medical device (100) may also receive and/or transmit relevant data information with one or more external medical related devices (405) as described later in greater detail in connection with FIGS. 6a and 6b.

FIG. 4b illustrates communication between a medical device (100) and a database server (403). The communication between the medical device (100) and the terminal (401) is like described in connection with FIG. 4a. Information/data received from the medical device (100) is transmitted by the terminal (401) to a server (403) preferably using the TCP/IP and PPP protocols and GPRS for high-speed data communication. Alternatively, a GSM or a UMTS network may be used. The server (403) may e.g. be an Internet database server. The server (403) receives the relevant information and stores it and determines what is to happen with the information e.g. where it/a copy is to be transmitted and/or stored, if and how it is to be processed, etc.

The server (403) may transmit the information to a number of mobile terminals (403) and/or computers (404) e.g. as an SMS message, an e-mail and/or in a suitable data format. Additionally, a computer (404) and/or a terminal (402) may also connect to the server (403) using standard browser software or WAP (Wireless application Protocol) in order to access, retrieve, etc. the relevant stored information, preferably, after specifying a valid password and user-name. In this way, either a client, a relative to a user and/or a medical professional may obtain easy access to the stored historical medical data and/or derivations (e.g. processed) thereof.

The secure socket layer (SSL)/transport layer security (TLS) may also be used by the communication devices in this system (one or more of terminal (401), terminal (402), the medical device (100), the server (403), the computer (404)) in order to enhance the security of the information. Bluetooth incorporates the possibility of using built-in security by finding devices, pairing devices, authentication, and encryption thereby enhancing the security between the medical device (100) and the terminal (401).

Applications of the embodiment shown in FIG. 4b corresponds to the applications described above in connection with FIG. 4a.

Yet another application of the present invention is that it may be used in connection of a clinical trial of a new medical product (new/modified drug, new measurement device, new drug administration device). Data collected by the medical device (100) and other related medical devices (405) may then be automatically transmitted directly to the relevant database server (403) for high-quality data storage and collection since the actual obtained data is obtained directly from the user/patient and transmitted e.g. for further processing. This may reduce the cost and the time-to-market of a new product since the data collection from many medical devices taking part in the medical trial may be automated. Additionally, the need for hand-written logs of the participants of the trial is avoided thereby eliminating possible typos and avoiding the need for manually inputting/scanning the logs into a system for storage and processing.

Alternatively, the mobile terminal (401) and/or the mobile terminal (402) may be an electronic device like a laptop, a PC, a PDA, etc. equipped with communication and/or a gateway (e.g. integrated, a network interface card (NIC), modem, etc.) to the Internet, a cellular network like a GSM, GPRS, UMTS network, etc. or another kind of communications network. The communication between the device (401) and the medical device (100) may e.g. be done via/according to the Bluetooth protocol or another RF communication protocol, IrDA (Inrared Data Association) protocols, a cable connection, etc.

One example of the use of the medical device (100) according to the present invention will be illustrated by the following use-case that describes a typical for a diabetic user equipped with a medical device (100) according to the invention.

At 7.00. The user gets out of bed and takes his cap unit with integrated BGM/medical device (100) and measures the glucose content of his blood.

The medical device (100) records this event with a time stamp and saves it in the memory/an electronic log book. Then the medical device (100) searches for a wireless access point (401) to the Internet, and if found, non-replicated data are transferred from the electronic log book to a server.

The user then decides to take x units of actrapid (making ready for his breakfast), he takes an insulin doser/insulin administration device (405) which he has already dedicated to be his actrapid doser and injects x units of actrapid. After the injection the actrapid doser (405) is placed in, docked with, brought in short-range communication range with, etc. the cap unit/medical device (100).

The doser (405) will now make contact to the cap/medical device (100) e.g. by means of an IR diode and an IR transistor to transfer dose size, insulin type, relative time stamp and doser status to the cap.

The cap/medical device (100) transfers setup data, if any, to the doser (405). The cap can now calculate the absolute time of this event and transfers it to the electronic log book.

The medical device (100) now searches for a wireless access point (401) to the Internet, and if found, non-replicated data are transferred from the electronic log book to a server (403).

At 8.00. The user has his breakfast.

At 9.00. The user arrives at his job, he decides (optionally the medical device (100) reminds him) to make a control measurement of the glucose content of his blood.

The medical device (100) records this event with a time stamp and saves it in the electronic log-book. The medical device (100) then searches for a wireless access point (401) to the Internet, and if found, non-replicated data are transferred from the electronic log-book to a server (403).

At 12.00. The user decides to measure the glucose content of his blood again.

The medical device (100) records this event with a time stamp and saves it in the electronic log-book. The medical device (100) then searches for a wireless access point (401) to the Internet, and if such an access point is found, non-replicated data are transferred from the electronic log-book to a server (403).

He now decides to take x units of actrapid (making ready for his lunch). After the injection he places his actrapid doser in the cap/medical device (100).

The doser (405) will now make contact to the cap/medical device (100) by means of an IR diode and an IR transistor to transfer dose size, insulin type, relative time stamp and doser status to the cap unit/medical device (100).

The cap/medical device (100) transfers setup data, if any, to the doser (405). The cap/medical device (100) can now calculate the absolute time of this event and transfers it to the electronic log-book.

The medical device (100) then searches for a wireless access point (401) to the Internet, and if such a point is found, non-replicated data are transferred from the electronic log-book to a server (403).

At 12.30. The user has lunch.

At 13.30. The user decides (optionally the medical device (100) reminds him) to make a control measurement of the glucose content of his blood.

The medical device (100) records this event with a time stamp and saves it in the electronic log book. The medical device (100) then searches for a wireless access point (401) to the Internet, and if found, non-replicated data are transferred from the electronic log book to a server (403).

At 17.00. The user decides to measure the glucose content of his blood again.

The medical device (100) records this event with a time stamp and saves it in the electronic log book. The medical device (100) then searches for a wireless access point (401) to the Internet, and if found, non-replicated data are transferred from the electronic logbook to a server (403).

He now decides to take x units of actrapid (making ready for his dinner). After the injection he places his actrapid doser (405) in the cap/medical device (100).

The doser (405) will now make contact to the cap/medical device (100) by means of an IR diode and an IR transistor to transfer dose size, insulin type, relative time stamp and doser status to the cap/medical device (100).

The cap/medical device (100) transfers setup data, if any to the doser (405). The cap/medical device (100) can now calculate the absolute time of this event and transfers it to the electronic log book.

The medical device (100) then searches for a wireless access point (401) to the Internet, and if is found, non-replicated data are transferred from the electronic log book to a server (403).

At 18.00. The user has his dinner.

At 19.00. The user decides (optionally the medical device (100) reminds him) to make a control measurement of the glucose content of his blood.

The medical device (100) records this event with a time stamp and saves it in the electronic log book. The medical device (100) then searches for a wireless access point (401) to the Internet, and if found, non-replicated data are transferred from the electronic log book to a server (403).

At 23.00. The user decides to go to bed. He measures the glucose content of his blood.

The medical device (100) records this event with a time stamp and saves it in the electronic log-book. The medical device (100) then searches for a wireless access point (401) to the Internet, and if such a point is found, non-replicated data are transferred from the electronic log-book to a server (403).

He now decides to take x units of insulatard (basic level for the night). He takes another doser (405) which he has already dedicated to be his insulatard doser and injects x units of insulatard. After the injection he places his insulatard doser (405) in/brings within short-range communication range of the cap/medical device (100).

The doser (405) will now make contact to the cap/medical device (100) by means of an IR diode and an IR transistor to transfer dose size, insulin type, relative time stamp and doser status to the cap/medical device (100).

The cap/medical device (100) transfers setup data, if any, to the doser (405). The cap/medical device (100) can now calculate the absolute time of this event and transfers it to the electronic log book.

The medical device (100) then searches for a wireless access point (401) to the Internet, and if found, non-replicated data are transferred from the electronic log book to a server (403).

The user possibly checks whether the medical device (100) contains non-replicated data, and if he finds that it is necessary to connect to his server, he activates a user menu in the medical device (100), which will immediately try to make contact to the server (403).

The medical device (100) then searches for a wireless access point (401) to the Internet, and if such an access point (401) is found, non-replicated data are transferred from the electronic log-book to a server (403).

Figure 5:
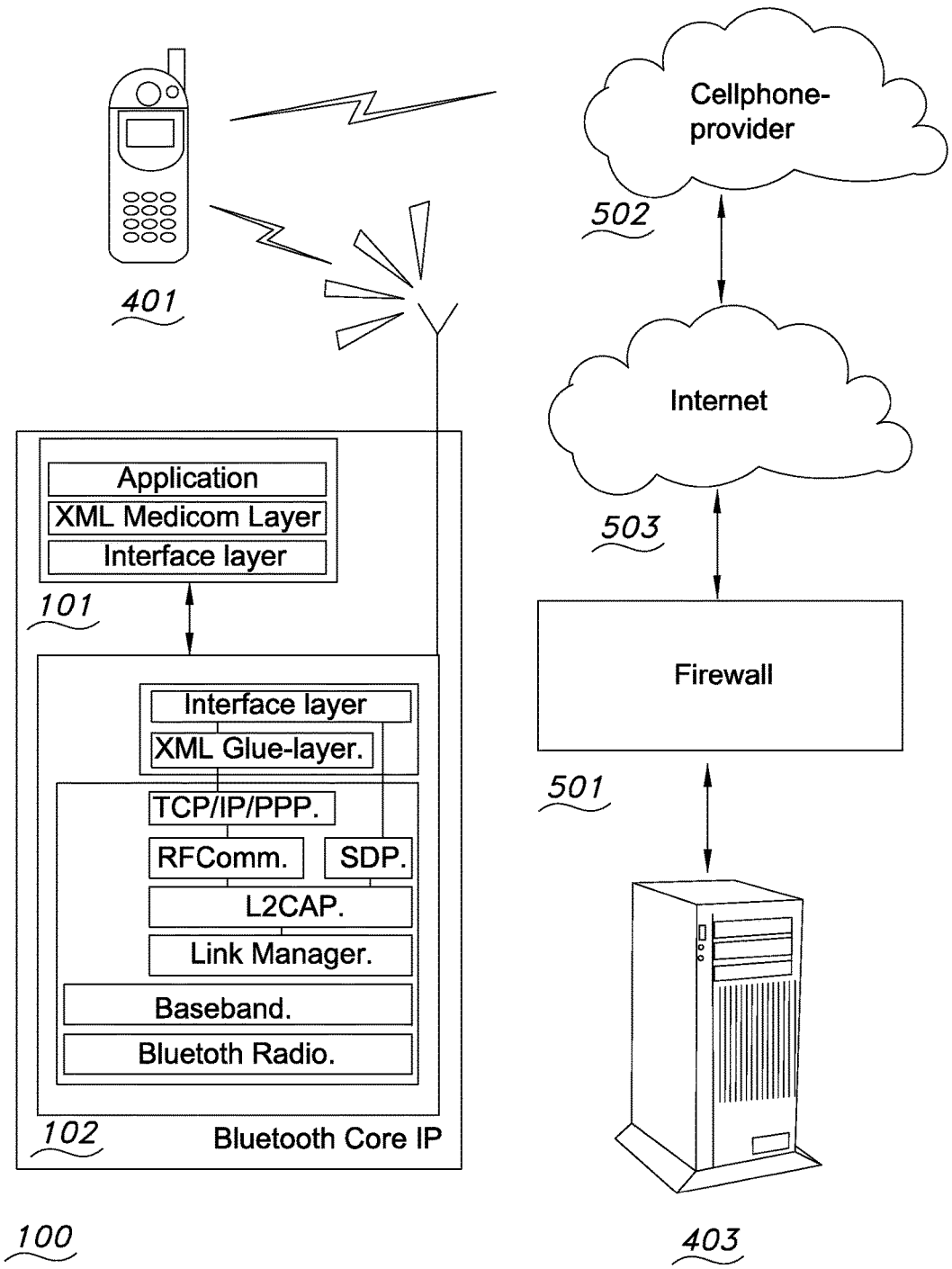
FIG. 5 illustrates the communication between a Bluetooth communication device part and a central Internet server.

FIG. 5 illustrates the communication between a Bluetooth communication device part and a central Internet server. Shown is a medical device (100) comprising a medical part (101) and a communication part (102) like described earlier. The communication part (102) comprises in this particular embodiment a Bluetooth communication core. The two parts (101; 102) is connected via an Interface Layer of each part so that the critical software, etc. handling the medical related function(s) of the medical device (100) is clearly separated. The medical related function(s) of the medical device (100) is illustrated by an Application Layer. The Interface Layer(s) connects and handles the two asynchronous systems/parts (101; 102) using polling by the medical part (101), assigned as master, of the communication part (102), assigned as a slave. In this way, the communication part (102) may not interfere, interrupt and/or transmit data/information to the medical part (101).

A XML Medicom Layer in the medical part (101) is also shown and is responsible for retrieving data/information to be transmitted from the memory of the medical part (101), calculate a check-sum (e.g. CRC) of the information and format it into a suitable format e.g. a XML format where the information e.g. is formatted into a number of frames each comprising a number of fields.

An example of fields in a frame for a given format is:

| Name of Data field | Length (chars) | Description |
| --- | --- | --- |
| DeviceID | 10 | 10 chars used for unique identification of the medical device. |
| DeviceVer | 4 | 4 chars used for definition of an actual XML-scheme used. |
| DeviceTime | 12 | A timestamp (e.g. mmddyyhhmmss). |
| FrameCount | 10 | Indicates FRAME number. |
| EventType | 12 | Indicates data type, etc. Note 1 |
| EventTime | 12 | A timestamp for a given event (e.g. mmddyyhhmmss). |
| EventSize | 4 | Value for event (e.g. amount of administered medication or value for measured medical value. |
| CheckSum | 8 | A calculated check-sum value for the information contained in the frame. |

In one example/embodiment events being communicated may be identified by:

Event_Type=INS-S-001 indicates an event where short-acting insulin of type 1 was administered.

Event_Type=INS-S-XXX indicates an event where short-acting insulin of type 'xxx' was administered.

Event_Type=INS-L-001 indicates an event where long-acting insulin of type 1 was administered.

Event_Type=INS-L-YYY indicates an event where long-acting insulin of type 'yyy' was administered.

Event_Type=INS-M-001 indicates an event where mix-acting insulin of type 1 was administered.

Event_Type=INS-M-ZZZ indicates an event where mix-acting insulin of type 'zzz' was administered, etc.

Event_Type=BGM-mmol/l indicates an event where a body fluid measurement/a blood glucose measurement (BGM) is done in mmol/1.

Event_Type=BGM-mg/dl indicates an event where a body fluid measurement/a blood glucose measurement (BGM) is done in mg/dl, etc.

Event_Type=BGM-mmol/l-k indicates an event where a calibration of a BGM/medical transducer is done in mmol/1.

Event_Type=BGM-mg/dl-k indicates an event where a calibration of a BGM/medical transducer is done in mg/dl, etc.

Event_Type=STRIPCODE indicates an event where a new strip-code, number identifier, bar-code, etc. for a given type of medication is inputted into the medical device (100).

Each Event_Type has an associated value (if applicable) specifying the actual value associated with the reported event. The range and resolution depends on the given event, e.g. may the values for a given type of medication/insulin cover the values 0-999 units (UI) with a resolution of $\frac{1}{10}$, a new strip-code may cover the values 0-999 with a resolution of 1, a calibration in mg/dl may cover 0-999 with a resolution of 1, a calibration in mmol/dl may cover 0-99 with a resolution of $\frac{1}{10}$, a BGM/body fluid measurement event in mg/dl may cover 0-999 with a resolution of 1, a BGM/body fluid measurement event in mmol/dl may cover 0-99 with a resolution of 1, etc.

The relevant information/frames is exchanged with the Bluetooth core like described in connection with FIG. 3 and transmitted to a Bluetooth supporting communication device/a mobile terminal (401) according to the Bluetooth protocol.

The relevant information/frames is sent via the mobile terminal (401) e.g. using GPRS, as described earlier, via a cell phone provider (502) and the Internet/a network (503) to a database server (403).

Preferably, a firewall (501) is connected between the Internet/the network (503) and the database server (403) in order to enhance the security of the server (403) by prohibiting unauthorised communication. The server (403) may be accessed and may process, transmit and/or receive information like described earlier.

Preferably, the server site also comprises a HTTP server connected between the firewall (501) and the database server (403) for handling requests from browsers according to the HTTP protocol.

The communication between the medical device (100) and the database server (403) may use encryption of communication and the web site (comprising the server(s)) may be secured using HTTPS/SSL (or HTTPS/TLS) communication.

The communication between the medical device (100) and the server (403) is preferably substantially a one-way communication (from the device to the server) (although necessary handshakes, receipts, etc. is transferred to the medical device (100)). If applicable, information, e.g. updated data/information, like recommended medical regimes, etc., is also transferred from the server (403) to the medical device (100).

Figure 6A:
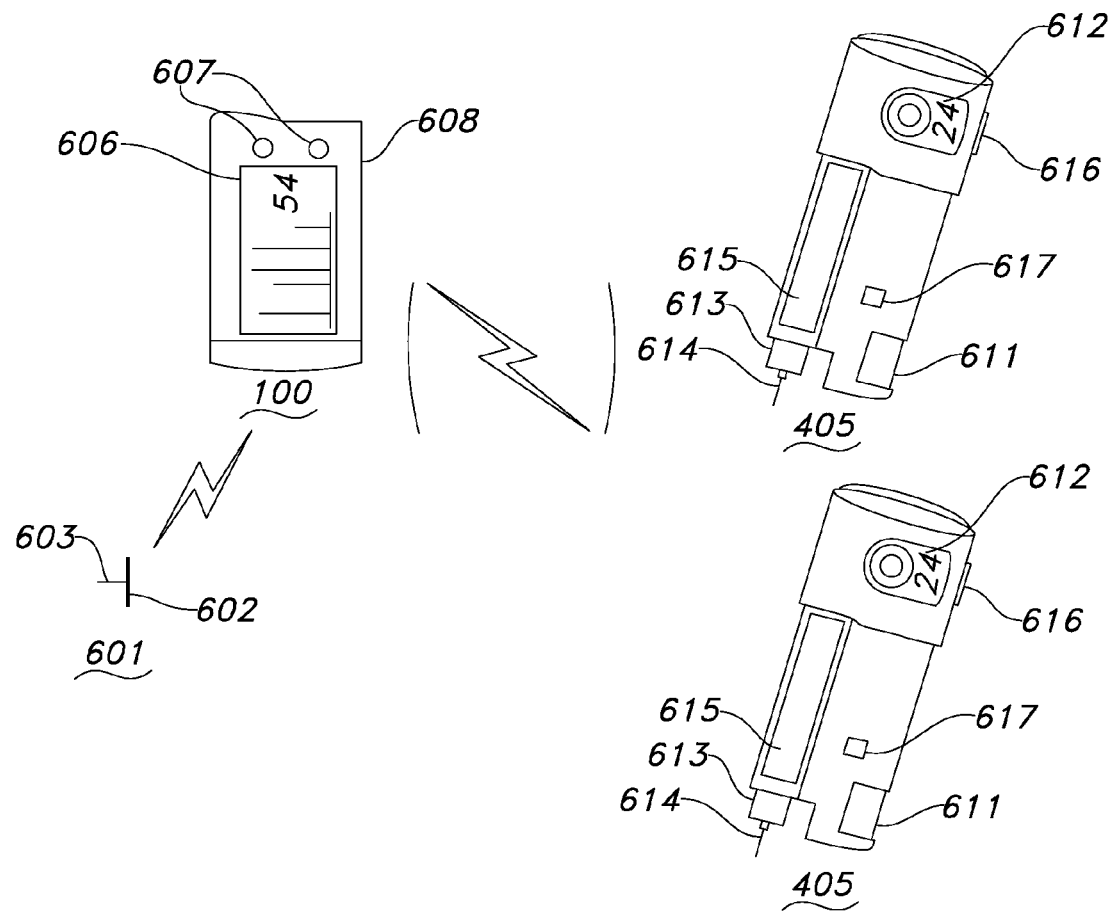
FIG. 6a illustrates the short-range communication between a medical device according to the present invention and other medical devices.

FIG. 6a illustrates the short-range communication between a medical device according to the present invention and other medical devices. Shown are a mobile medical device (100), two additional medical devices that in this particular example are two drug administration devices (405) containing different types of medication, e.g. fast- and slow-acting insulin, and a CGM/biosensor (601) like a glucose biosensor.

The dosers (405) comprises input means e.g. a turning wheel (611) for adjusting, either electronically or manually, the level/amount of medication to be administered, activation/input means (616) for initiating the administration of medication and a display (612) that shows the currently selected amount of medication to be administered with text, icons, graphic representations, etc. The doser (405) preferably has processing means and storage facilities, like a CPU and RAM, for processing and storing data, like the time, date and amount of medication of the last couple of administrations. This information can be shown in the display (612) e.g. on request.

The doser (405) further comprises a cartridge (613) that contains the medication to be administered, and is fitted with a needle (614) through which the medication is administered. The doser (405) has a transparent window (615) so that the amount of medication left in the cartridge (613) can readily be identified.

Cartridges (613) may contain different types of insulin, like fast and slow acting insulin, a mix-acting, etc., and the user may insert/exchange a cartridge (613) of a given type when needed and/or use multiple dosers (405) with different types of medication (e.g. fast-acting and slow-acting insulin).

The dosers (405) are also provided with short-range communications means (617) for receiving and transmitting information and data representations from and to other devices as will be described in the following. Alternatively, a doser (405)/an additional medical device (405) may be provided with wireless communications means/a wireless transceiver, as indicated by the arrow in parenthesis, instead or in combination with the short-range communications means (617).

The CGM (601) is a device that monitors/measures the blood glucose level/concentration of a user continuously and comprises, in this embodiment, a base unit and a glucose biosensor (603).

The CGM base unit is in this embodiment the medical device (100) or more specifically the medical device part (101) being in communication with the biosensor (603). Alternatively, a separate CGM base unit may be provided that communicates with the medical device (100).

The glucose biosensor (603) is mounted on an adhesive (602) located on an appropriate part of the user's body like the stomach, upper arm, etc. and is located subcutaneous, i.e. in the external fat, in the user's body.

The biosensor (603) preferably comprises a potentiostat where a fixed potential can be applied between two electrodes of the biosensor hereby measuring the current that the work electrode of the biosensor produces. The generated current is proportional to the glucose concentration in the blood of the user.

The generated current is transmitted via a wire/cable or wireless communication means like IR transceivers, RF transceivers, etc. to the CGM base unit (100) for a translation/interpretation from a continuous signal into a representation for later processing. Preferably this translation is performed by a standard A/D converter with a sampling rate which at least is faster than the worst case change of the BGL so even the fastest change is 'captured' by the CGM (601)/CGM base unit (100). A sampling rate may e.g. be once every couple of minutes.

Alternatively, the sampling takes place at the biosensor (601) and only the sampled values are transmitted to the CGM base unit (100).

The converted measurement/continuous values may be presented to the user via displaying means (606) like a LCD display, etc.

The converted measurements are kept in a memory for later retrieval, analysis, and etc. so a detailed history log of sampled measurements may be obtained. This detailed history log may e.g. be used to predict a trend for the BGL of a user thereby enhancing the information value for the user.

In one embodiment the BGL measurement is converted into a corresponding amount of insulin needed to bring the user into compliance and displayed on the display (606).

The biosensor (603) is preferably calibrated on a regular basis, e.g. each day, by external calibration e.g. by a traditional blood glucose monitor (BGM) system, in order to ensure the best accuracy. Typically the biosensor (603) will have to be replaced after e.g. three days of use and be calibrated once each day.

Alternatively, the CGM may be embodied by other invasive, semi-invasive or non-invasive systems.

In a preferred embodiment, the medical device (100) is a protective cap unit comprising an integrated blood glucose monitor (BGM), and one additional medical device (405) is an insulin administration device arranged so that they automatically transmit, via short-range communications means, relevant data information between them when the devices are mutually positioned in a suitable communication position, e.g. when the cap unit/the medical device (100) is fitted onto, docked with/onto, clicked-on, screwed-into, snapped-with, etc. with the additional medication device (405).

Alternatively, the additional medication device (405) may be another type of drug administration device like a pen, syringe, inhaler, tablet dispenser, etc. or in general any medication administration device.

In this way, simplicity for the user is obtained, since the devices automatically store and exchange data information as part of the normal use.

The cap unit/medical device (100) can be fitted to an additional medication device (405) so that one single compact unit and protection of the additional medication device (405) is obtained.

In this way, the user does not have to worry about collecting data information in a separate log-book and additionally, the data information may be collected in a single apparatus for further processing, transmission and/or use. In this way, a complete log-book is obtained in e.g. a single device, which may be used by the user with the help of the devices to obtain detailed information of trends, current and/or previous state(s), re-occurring events, e.g. that adverse effects relating to the self-treatment occur every Sunday by using/analysing for behavioural and/or measured physiological patterns.

The short-range communications means (617) is preferably an infrared (IR) communications means/transceiver providing IR communication of data information between the medical device (100) and the additional medication device (405).

Alternatively, the short-range communications means (617) is an inductive means i.e. comprising inductive coils or the like in each device.

As another alternative, the short-range communications (617) is a electrical communications means, i.e. a simple switch mechanism that may be used to transfer data information between devices.

The embodiments of the short-range communication means (617') are explained in greater detail in connection with FIGS. 7a-7c.

Additionally, the energy/power used for communication between the apparatuses is minimized and/or reduced since only (very) short-range communication needs to be used when the cap/medical device (100) is fitted on, etc. to the additional medication device (405). This is very important, especially for portable apparatuses, since reduced energy consumption extends the time between the need for charging a power source of the apparatuses, like a battery, etc., prolongs the time where the apparatuses may be used and/or extends the life-time of a non-chargeable power source.

Figure 6B:
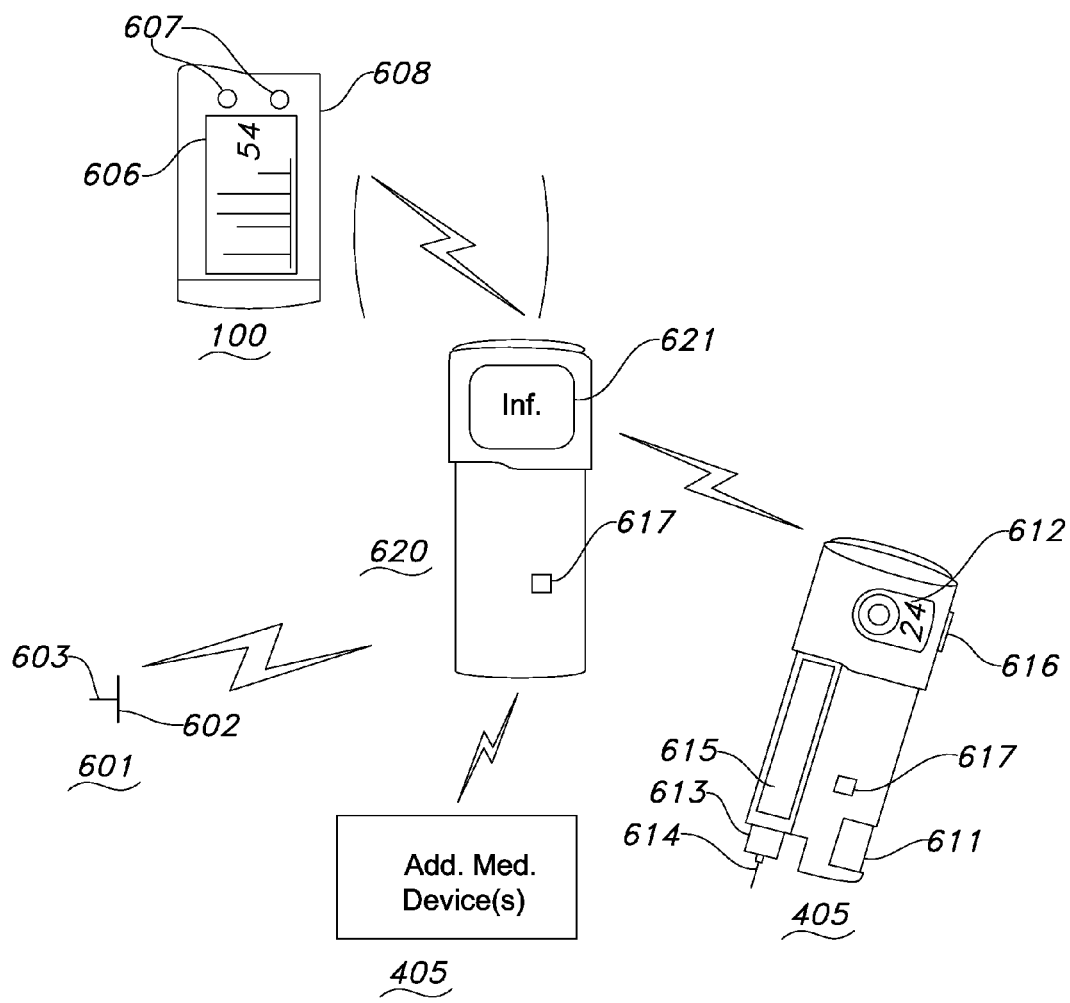
FIG. 6b illustrates communication between a medical device according to the present invention and other medical devices.

FIG. 6b illustrates communication between a medical device according to the present invention and other medical devices. Shown are a medical device (100) according to the present invention, a CGM biosensor (601), a drug administration device (405), a schematic representation of additional medical device(s) (405), and a general base unit (620).

The general base unit (620) comprises a display (621), a user interface and, preferably, wireless communication means/a wireless transceiver for collecting and/or exchange relevant data information from the other devices (601, 405). The information may be viewed at the display (621) and stored at the base unit (620) and be transmitted to the medical device (100) using short-range communication means (617) when docking, fitting, clicking-on, screw-into, snap-with, etc. the medical device (100) and the base unit (620), as described earlier. Alternatively, the base unit (620) and the medical device (100) is provided with wireless communications means/a transceiver instead or in addition to the short-range means (617), as indicated by the arrow in parenthesis.

The additional medical device(s) (405) may comprise a tablet dispenser, inhaler, a balance, body fluid measure device, drug administration device or in general other diabetes relevant data sources.

In this way, an easy way of obtaining additional information from various other relevant devices is provided.

FIGS. 7a-7d illustrate examples of various embodiments of the short-range communication means.

Figure 7A:
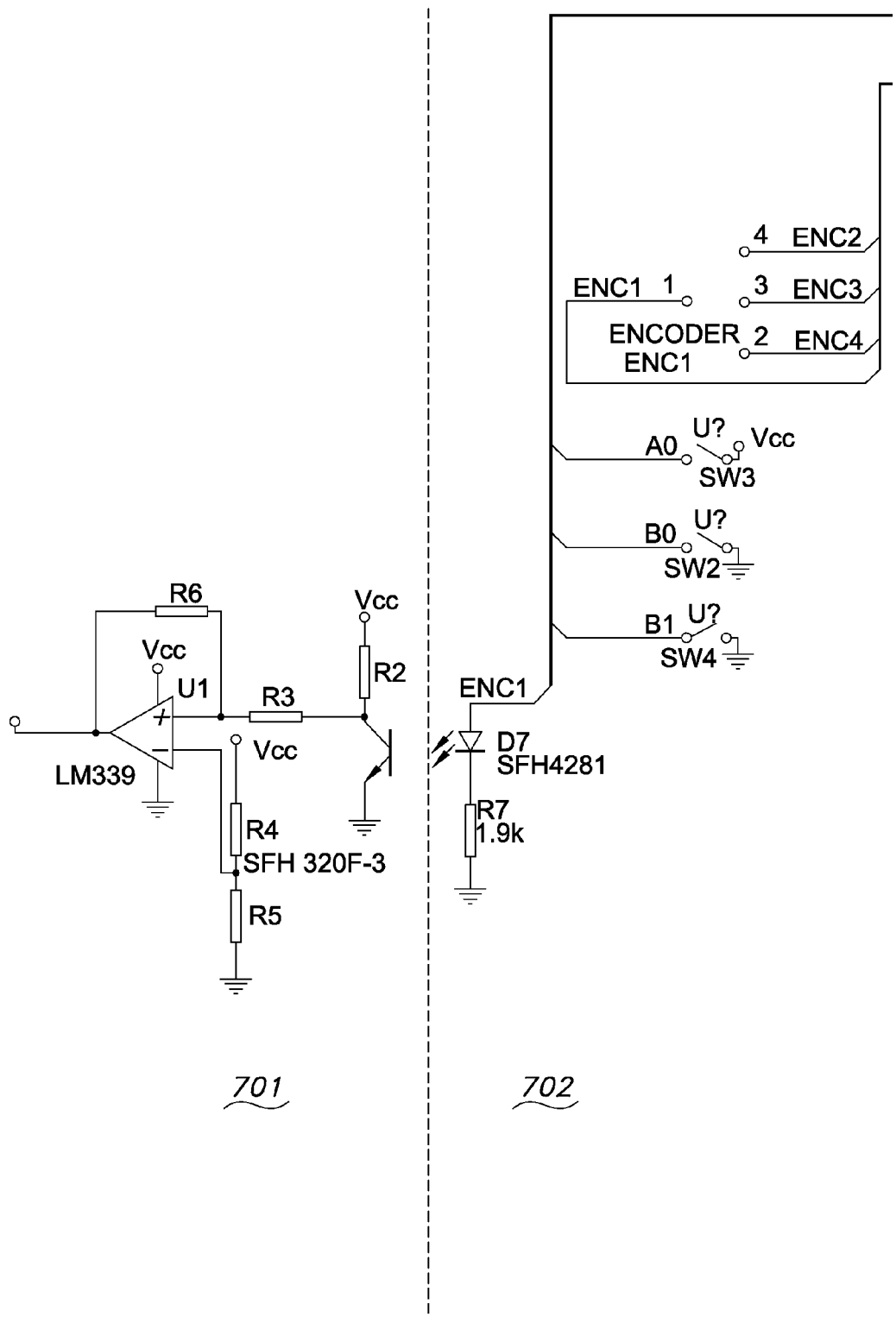
FIGS. 7a-7d illustrate examples of various embodiments of the short-range communication means.
Figure 7B:
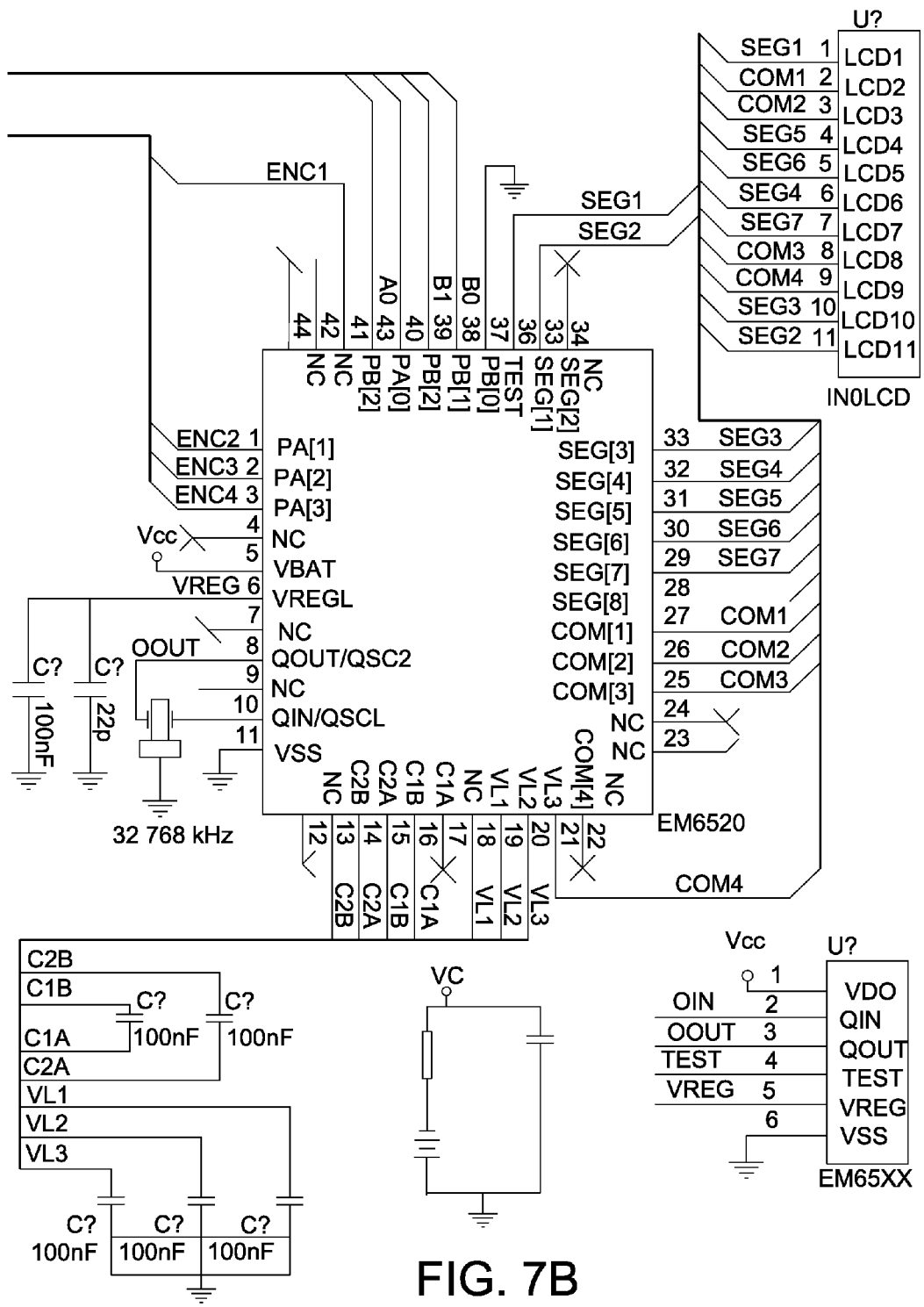

FIG. 7a-7b illustrate an embodiment of the short-range communication means adapted to communicate optically. Shown is an example of an embodiment of infrared (IR) communication means/transceivers. Shown are a receiver part (701) of the medical device part and a transmitter part (702) of an additional medical device. Alternatively, the medical device part and additional medical device is each provided with a receiver (701) and a transmitter (702) thereby enabling two-way communication.

Figure 7C:
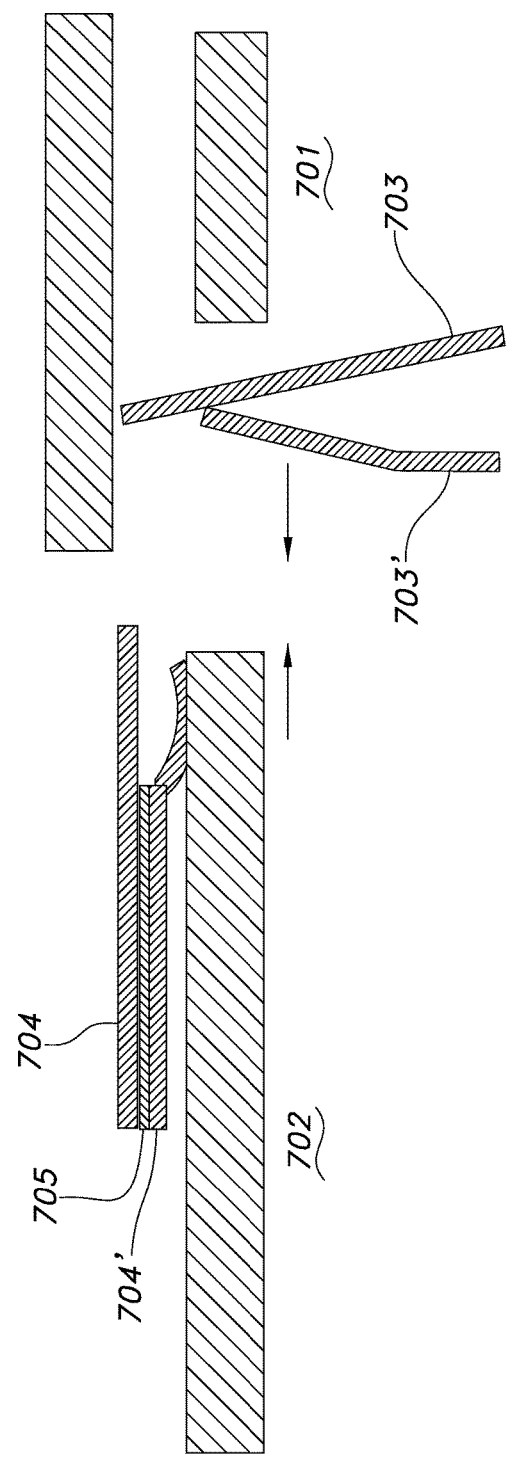

FIG. 7c illustrates an embodiment of the short-range communication means adapted to communicate via an electrical switch. Shown is a cross-sectional view of an example of an embodiment of simple mechanical/electrical communication means in the form of switches. Shown are the communication switches of a medical device part (701) and of an additional medical device (702). The communications switches (703; 703') of the medical part (701) have an electric connection between them when the medical device part and additional device (701; 702) is not docked, fitted onto, in an interrelated communication position, etc. When the two devices (701; 702) are brought together then a first switch/switch part (704) of the additional device (702) touches and moves the first switch/switch part (703) of the medical device part (701) thereby establishing an electronic connection between them (703, 704) and breaking the connection of switch/switch part (703) and (703'). During the same movement a second switch/switch part (704') of the additional device (702) touches the second switch/switch part (703') of the medical device part (701) thereby establishing an electronic connection. The breaking of the connection between the first switch/switch part (703) and the second switch/switch part (703') may determine when communication, transfer of information, etc. may be initiated.

The first (704) and second switch/switch part (704') of the second apparatus is preferably separated by an insulation layer (705).

Figure 7D:
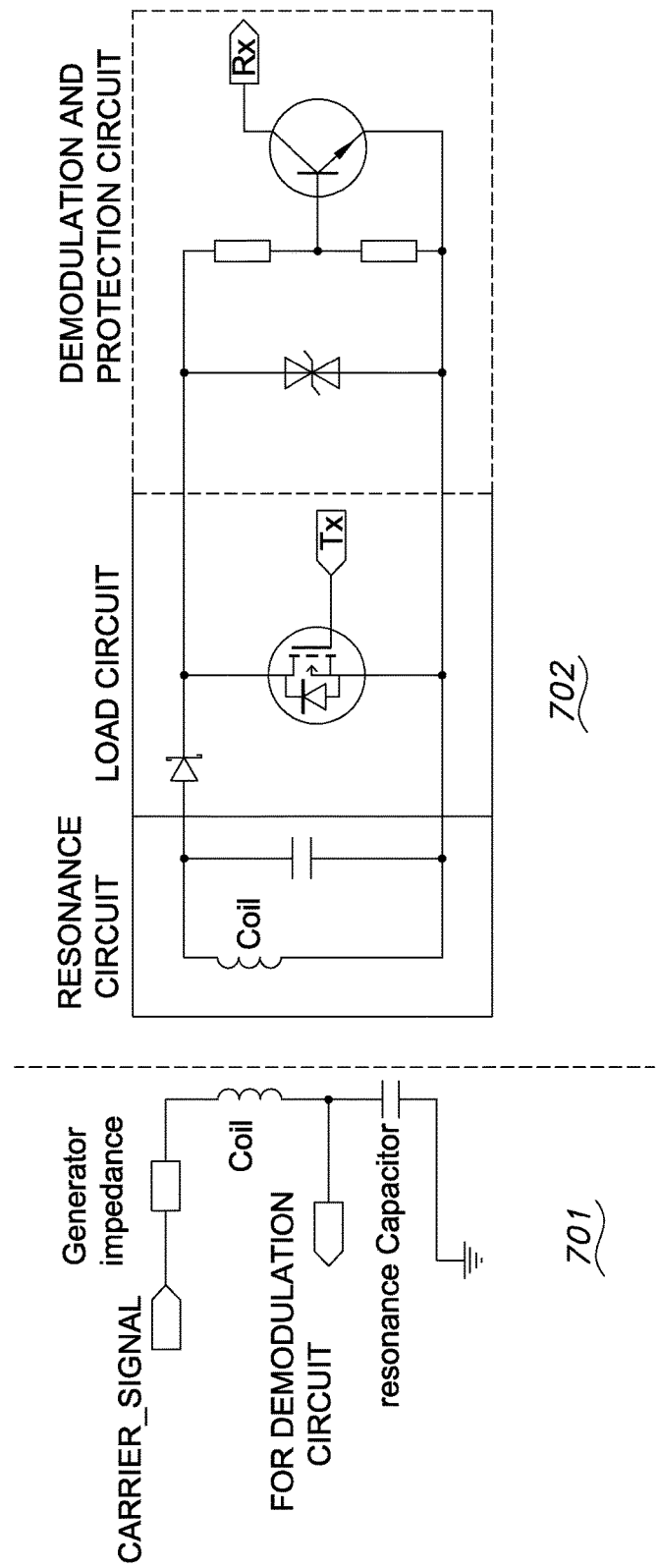

FIG. 7d illustrates an embodiment of the short-range communication means adapted to communicate via inductive communication. Shown is an example of an embodiment of simple inductive communication means where current induced in a resonance circuit is used to transfer information. Shown are a receiver part (701) of a medical device part and a transmitter part (702) of an additional medical device. Alternatively, the medical device part and the additional medical device is each provided with a receiver (701) and a transmitter (702) thereby enabling two-way communication.

What is claimed is:

1. A method of communicating medical data information of a portable unitary integrated medical device, the method comprising:
    providing the portable unitary integrated medical device comprising:
        a medical part comprising:
            at least one apparatus selected from the group consisting of:
                a discrete or substantially continuous body fluid analysis apparatus structured to monitor one or more bodily parameter(s), and
                a drug administration apparatus structured to administer or direct administration of an agent to a patient,
            a first processor,
            a first storage apparatus, and
            a first physical interface; and
        a communication part comprising:
            a second processor,
            a second storage apparatus,
            a communication apparatus configured for communication with at least one other medical device, and
            a second physical interface;
    internal exchanging of the data information between the medical part and the communication part; and
    external exchanging of the data information between the communication part and the at least one other medical device;
    wherein:
        the medical part and the communication part are unitary physically integrated and connected via their respective first and second physical interfaces and the internal exchanging occurs only according to a predetermined protocol, functionalities of each of the medical and communication parts otherwise being separate;

the predetermined protocol comprises the medical part acting as a master and the communication part acting as a slave, such that:
the internal exchanging is initiated and controlled by the medical part solely; and
the external exchanging is performed by the communication part solely.

2. The method according to claim 1, wherein the medical part complies with preset validation standards for medical devices, the communication part complies with preset validation standards for communication devices, and wherein the communication part is able to be interchanged with a second communication part without affecting the medical part's compliance with the preset validation standards for medical devices.

3. The method according to claim 1, wherein the medical part further comprises one or more of:
a user interface, and
at least one medical transducer.

4. The method according to claim 1, wherein the at least one other medical device is selected from the group of:
a drug administration device,
a body fluid analyzer,
an insulin administration device,
a blood glucose monitor (BGM),
a continuous blood glucose monitor (CGM),
an inhaler,
a tablet dispenser,
a lipid monitor,
a pulse monitor,
a lancet device,
a storage container,
a balance,
another said portable unitary integrated medical device and
any other apparatus adapted to measure at least one physiological parameter.

5. The method according to claim 1, wherein the method further comprises controlling a power supply by the medical part, where the power supply supplies the communication part with power, and where the power supply may be turned on and off under the control of the medical part.

6. The method according to claim 1, wherein the communication part communicates according to the IEEE 802.15.1 protocol.

7. The method according to claim 1, wherein the communication part communicates information according to one or more of:
Radio frequency (RF) communication,
Infrared (IR) communication,
HTTP (Hyper Text Transmission Protocol),
SHTTP (Secure Hyper Text Transmission Protocol),
TCP/IP (Transmission Control Protocol/Internet Protocol),
PPP (Point-to-Point),
SSL (Secure Socket Layer),
TLS (Transport Layer Security),
short-range communication, and
IrDA.

8. The method according to claim 1, wherein the communication part communicates with a wireless access point and/or a mobile terminal, where the access point and/or the terminal communicates according to one or more of:
GSM (Global System for Mobile communication),
GPRS (General Packet Radio System), and
UMTS (Universal Mobile Telephone System).

9. The method according to claim 1, wherein the communication part exchanges data information with a central server via a wireless network access point.

10. The method according to claim 1, further comprising:
automatically transmitting the data information from the communication part to a central server for storage in at least one database,
processing the data information, in order to derive additional information, and
automatically transmitting at least a part of the additional information to a predetermined third party selected from the group consisting of:
at least one of a relative,
at least one parent, and
at least one medical professional.

11. The method according to claim 10, wherein said processing is done at said server and/or at said portable medical device.

12. The method according to claim 10, wherein said data information comprises information representing one or more of:
at least one blood glucose value,
at least one value representing a body fluid level,
at least one physiological parameter,
amount and/or type of administered medication,
amount and/or type of administered insulin,
a trend of a glucose or body fluid level,
a prediction of a glucose or body fluid level,
timestamp in- or excluding date,
amount of food,
measurement of physical activity,
notification of appointment,
inventory logistics,
body characteristics,
warnings, and
symptoms.

13. The method according to claim 10, wherein the transmitting data information from the communication part to the central server is done by transmitting the data information according to the IEEE 802.15.1 protocol to a wireless access point connected via a network to the central server.

14. The method according to claim 13, wherein said method further comprises retrieving relevant data information from the at least one other medical device.

15. A portable medical device for communication of medical data information, the device comprising:
a medical part comprising:
at least one apparatus selected from the group consisting of:
a discrete or substantially continuous body fluid analysis apparatus structured to measure one or more bodily parameter(s), and
a drug administration apparatus structured to administer or direct administration of an agent to a patient,
a first processor and first storage apparatus, and
a first physical interface; and
a communication part comprising:
a second processor,
a second storage apparatus, a communication apparatus, configured for communication with at least one other medical device and external exchange of their data information, and a second physical interface;

wherein:

the medical part and the communication part are unitary and physically integrated and connected via their respective first and second physical interfaces and internal exchange of the data information between one another occurs only according to a predetermined protocol, functionalities of each of the medical and communication parts otherwise being separate;

the predetermined protocol comprises the medical part acting as a master and the communication part acting as a slave, such that:

the internal exchange initiated and controlled by the medical part solely; and the external exchange is performed by the communication part solely.

16. The portable medical device according to claim 15, wherein the medical part complies with preset validation standards for medical devices, the communication part complies with preset validation standards for communication devices, and wherein the communication part is structured to be interchanged with a second communication part without affecting the medical part's compliance with the preset validation standards for medical devices.

17. The portable medical device according to claim 15, where the communication part is further adapted to:

automatically transmit data information from the portable medical device to a central server for storage in at least one database, process said data information, in order to derive additional information, and automatically transmit at least a part of the additional information to a predetermined third party selected from the group consisting of:
at least one medical professional,
at least one relative, and
at least one parent.

18. The medical device of claim 17, wherein the medical part further comprises hardware comprising a computer readable medium encoded with a computer program, wherein the computer program comprises at least one of software or firmware.

19. The medical device according to claim 17, wherein said processing is done at said server and/or at said medical device.

20. The medical device according to claim 17, wherein said data information comprises information representing one or more of:
at least one blood glucose value,
at least one value representing a body fluid level,
at least one physiological parameter,
amount and/or type of administered medication,
amount and/or type of administered insulin,
a trend of a glucose or body fluid level,
a prediction of a glucose or body fluid level,
timestamp in- or excluding date,
amount of food,
measurement of physical activity,
notification of appointment,
inventory logistics,
body characteristics,
warnings, and
symptoms.

21. The medical device according to claim 17, wherein the communication part is structured to transmit data information according to the IEEE 802.15.1 protocol from the communication part to a wireless access point connected via a network to the central server.

22. The medical device according to claim 17, wherein the communication part is further configured to retrieve relevant data information the at least one other medical device.

23. The system for collecting data information from a number of portable devices according to claim 15, wherein the system is structured to:

generate data information in at least one of the portable devices, the data information relating to a clinical trial of the medical part and/or medical product, automatically send the data information from the communication part to a central server for storage in a database, and process said data information.

* * * * *